US010555857B2

(12) United States Patent
Anderberg et al.

(10) Patent No.: US 10,555,857 B2
(45) Date of Patent: Feb. 11, 2020

(54) FLEXIBLE MEDICAL SUPPORTS

(71) Applicant: ARJO IP HOLDING AB, Malmo (SE)

(72) Inventors: Mimmi Anderberg, Lund (SE); Per Ekelin, Trelleborg (SE); Marcus Johansson, Hjarup (SE); Marie Rubin, Barseback (SE); Thomas Nilsson, Staffanstorp (SE); Karolina Nilsson, Sondra Sandby (SE)

(73) Assignee: Arjo IP Holding AB, Malmö (SE)

( * ) Notice: Subject to any disclaimer, the term of this patent is extended or adjusted under 35 U.S.C. 154(b) by 64 days.

(21) Appl. No.: 14/866,954

(22) Filed: Sep. 26, 2015

(65) Prior Publication Data

US 2016/0184151 A1   Jun. 30, 2016

Related U.S. Application Data

(63) Continuation-in-part of application No. PCT/EP2014/055912, filed on Mar. 25, 2014.

(30) Foreign Application Priority Data

Mar. 26, 2013   (EP) ..................................... 13161046

(51) Int. Cl.
*A61G 7/10* (2006.01)
*A61G 5/12* (2006.01)
(Continued)

(52) U.S. Cl.
CPC .............. *A61G 7/1096* (2013.01); *A61F 5/37* (2013.01); *A61F 5/3738* (2013.01);
(Continued)

(58) Field of Classification Search
CPC . A61G 5/14; A61G 5/127; A61G 5/12; A61G 5/10; A61G 7/1038; A61G 7/1049;
(Continued)

(56) References Cited

U.S. PATENT DOCUMENTS 909,411 A * 1/1909 Hockney ................ A47C 4/283
297/423.26
2,005,294 A   6/1935 Lazare
(Continued)

FOREIGN PATENT DOCUMENTS

CN    1788705 A    6/2006
CN  201814751 U   5/2011
(Continued)

OTHER PUBLICATIONS

International Search Report for PCT/EP2014/055912, dated Jun. 12, 2014, European Patent Office, Netherlands, 4 pages.

*Primary Examiner* — David R Hare
(74) *Attorney, Agent, or Firm* — The Webb Law Firm (57) ABSTRACT

A patient support is provided with a membrane made of a stretchable material. The membrane may be fixed in one embodiment to lateral supports and used as a patient's knee or calf support. During use, the membrane can stretch on the application of force by a patient, which stretch will reduce discomfort and pain and can also assist in preventing slippage of the patient during movement. The flexible membrane may be used also in patient slings and other supports.

20 Claims, 9 Drawing Sheets

(51) Int. Cl.
  *A61G 5/10* (2006.01)
  *A61F 5/37* (2006.01)
  *A61G 5/14* (2006.01)
(52) U.S. Cl.
  CPC .............. *A61F 5/3776* (2013.01); *A61G 5/10* (2013.01); *A61G 5/12* (2013.01); *A61G 5/127* (2016.11); *A61G 5/14* (2013.01); *A61G 7/1038* (2013.01); *A61G 7/1051* (2013.01)
(58) Field of Classification Search
  CPC ... A61G 7/1051; A61G 7/1096; A61F 5/3776; A61F 5/3738; A61F 5/3792; A61F 5/3784; A61F 5/37
  See application file for complete search history.

(56) References Cited

U.S. PATENT DOCUMENTS

| | | | | |
|---|---|---|---|---|
| 2,609,864 A * | 9/1952 | Gates, Jr. | | A61G 5/12 297/423.19 |
| 3,041,636 A * | 7/1962 | Twedt | | A61G 7/1017 297/5 |
| 3,098,479 A * | 7/1963 | Storey | | A61F 5/3784 128/874 |
| 3,669,107 A * | 6/1972 | Posey | | A61G 5/1054 128/845 |
| 3,669,493 A * | 6/1972 | Vowles | | A47C 4/12 297/423.11 |
| 3,863,984 A * | 2/1975 | Sickels | | A61G 5/12 297/423.17 |
| 3,884,225 A * | 5/1975 | Witter | | A61G 7/065 128/876 |
| 4,065,180 A * | 12/1977 | Karay | | A61G 5/10 297/466 |
| 4,157,593 A * | 6/1979 | Kristensson | | A61G 7/1019 5/87.1 |
| 4,192,546 A * | 3/1980 | Smith | | A61G 5/10 297/423.17 |
| 4,435,863 A * | 3/1984 | Lerich | | A61G 7/1017 280/304.1 |
| D279,362 S * | 6/1985 | Sink | | D12/133 |
| 4,682,377 A * | 7/1987 | Reich | | A61G 7/1017 5/83.1 |
| 4,695,072 A * | 9/1987 | Brooks | | A61G 1/013 280/47.25 |
| 4,948,156 A * | 8/1990 | Fortner | | A61G 5/14 180/907 |
| 5,062,677 A * | 11/1991 | Jay | | A61G 5/12 297/440.2 |
| 5,093,944 A * | 3/1992 | Winston, Sr. | | A61G 7/1017 280/47.25 |
| 5,189,741 A * | 3/1993 | Beardmore | | A61G 7/1017 5/81.1 R |
| 5,233,708 A * | 8/1993 | Winston, Sr. | | A61G 7/1038 280/47.25 |
| 5,542,690 A | 8/1996 | Kozicki | | |
| 5,950,258 A * | 9/1999 | Deyne | | A61G 7/10 135/66 |
| 6,083,182 A | 7/2000 | Fries | | |
| 6,168,238 B1 * | 1/2001 | Hannagan | | A61G 5/12 297/423.3 |
| 6,389,619 B1 * | 5/2002 | Dunn | | A61G 7/1017 5/81.1 R |
| 6,430,761 B1 * | 8/2002 | Brandorff | | A61G 7/053 5/81.1 R |
| 6,568,003 B1 * | 5/2003 | Vest | | A61G 7/1015 5/81.1 R |
| 7,356,858 B2 * | 4/2008 | Summers | | A61G 7/1015 5/83.1 |
| 7,627,912 B1 * | 12/2009 | McKinney | | A61G 7/1011 5/81.1 R |
| 8,291,535 B2 * | 10/2012 | Kemper | | A61G 5/1043 297/452.27 |
| 8,443,473 B2 * | 5/2013 | Maxwell | | A61G 7/1038 5/648 |
| 8,882,129 B2 * | 11/2014 | Nault | | A61G 5/12 280/304.1 |
| 9,095,484 B1 * | 8/2015 | Bethea | | A61G 5/12 |
| 9,295,597 B2 * | 3/2016 | Hjort | | A61G 5/14 |
| 9,532,914 B1 * | 1/2017 | Nichols | | A61G 7/1023 |
| 2005/0274388 A1 | 12/2005 | Kosh | | |
| 2008/0272573 A1 * | 11/2008 | Hiatt | | A61G 5/1054 280/304.1 |
| 2009/0113623 A1 * | 5/2009 | Thomas | | A61G 7/1023 5/89.1 |
| 2009/0144894 A1 * | 6/2009 | Shiffert | | A61G 7/1038 5/81.1 T |
| 2010/0095459 A1 * | 4/2010 | Lambert | | A61G 5/127 5/653 |
| 2010/0117436 A1 * | 5/2010 | Kimball | | A61G 5/10 297/466 |
| 2012/0146301 A1 | 6/2012 | Horvath et al. | | |
| 2014/0345625 A1 * | 11/2014 | Abdoli-Eramaki | | A61F 5/37 128/845 |

FOREIGN PATENT DOCUMENTS

| | | | | |
|---|---|---|---|---|
| EP | 2522317 A2 | 11/2012 | | |
| JP | WO 9611658 A1 * | 4/1996 | ........... | A61G 7/1017 |
| JP | 09238983 A | 9/1997 | | |
| JP | H09238983 A | 9/1997 | | |
| JP | H09570 U | 12/1997 | | |
| JP | 2003169826 A | 6/2003 | | |
| JP | 2006263314 A | 10/2006 | | |
| JP | 2008246197 A | 10/2008 | | |
| JP | 2010246635 A | 4/2010 | | |
| JP | 2011161190 A | 8/2011 | | |
| JP | 2011217882 A | 11/2011 | | |
| WO | WO 9518592 A1 * | 7/1995 | ........... | A61G 7/1017 |
| WO | 20050120423 A1 | 2/2005 | | |

* cited by examiner

Figure 9

FLEXIBLE MEDICAL SUPPORTS

This is a continuation-in part application of International Patent Application No. PCT/EP2014/055912 filed on Mar. 25, 2014, pursuant to 35 U.S.C. 356(c), which in turn claims benefit of priority to EP Application No. 13161046.1 filed on Mar. 26, 2013, all the disclosures of which are herein incorporated by reference in their entirety.

1. FIELD OF THE INVENTION

The present application relates to flexible patient supports which are made from or incorporate flexible support sheets or panels.

2. BACKGROUND OF THE INVENTION

Various types of patient supports are used for lifting a patient from a sitting or reclining position or for moving a patient. Examples include harnesses, sit-to-stand supports, and the like. Typically, such supports are made of hard and/or inelastic materials, for instance metal and/or canvas, designed for load bearing support that are uncomfortable and/or may be abrasive, tearing into a patient's skin.

In cases where a patient is to be raised from a sitting position, it is sometimes advantageous or necessary to hold the patient's knees and/or ankles to prevent the patient from slipping. For this purpose, it is known to provide knee or ankle supports that support and/or facilitate the appropriate positioning of a patient's knees, shins or ankles. As the patient rises to a standing position, the knees, shins or ankles press against the supports to assist the patient in rising. Often significant pressure is applied by the patient's knees, shins or ankles on the supports. Such supports are typically constructed from metal plates covered in foam or soft plastic. The hard support material of these leg or knee supports, however, focuses stress on the knees and knee caps and can be uncomfortable despite the foam/plastic covering.

Similarly, conventional slings and harnesses as used in patient lifts are generally constructed from inelastic material, such as canvas or a stiff fabric, and need to be manually adjusted to conform to and secure a patient. They also have seams and stitch lines at its edges and along contoured regions of such supports which can be relatively hard, causing discomfort, chaffing and grazing the patient.

SUMMARY OF THE INVENTION

The present application is directed to improved patient supports that may be used in association with and/or incorporated in various medical devices and/or systems.

In accordance with an exemplary embodiment of the present application, there is provided a patient support including at least one support membrane made of stretchable material.

In accordance with an exemplary embodiment, the membrane is formed from a sheet material. In another embodiment, the membrane is moulded to a predetermined shape, typically contoured for a person.

In accordance with an exemplary embodiment, the membrane is formed from silicone. In other embodiments, the membrane is formed from polyurethane, thermoplastic polyurethane (TPU), a thermoplastic elastomer (TPE), rubber or a rubber-like material.

In accordance with an exemplary embodiment the membrane may be formed from a stretchable fabric.

In accordance with an exemplary embodiment, the patient support includes a support structure, to which the membrane is connected. Advantageously, the membrane may be connected to the support structure only at edges or extremities thereof. It will be appreciated that with such a structure, the membrane can flex while on and/or attached to the support structure. In this regard, is the membrane can be configured as a freestanding membrane in which no component of the assembly is disposed behind or contacts the operative side of the membrane during use permitting the membrane to flex without causing the patient to come into contact with any other part of the support, such as a metal plate as occurs with existing knee supports. The membrane is thus free to flex on the support structure.

In accordance with an exemplary embodiment, the support structure provides a lateral frame across which the membrane is connected. The lateral frame may include first and second side elements to which the membrane is connected, where edges of the membrane between the lateral frames are able to flex.

In accordance with an exemplary embodiment, the patient support is a knee/leg support, shin support or an ankle support. In another embodiment, the patient support is a sling.

In accordance with an exemplary embodiment, the membrane is free of stitching where the body is placed, for instance free of stitching save for at a support structure.

In accordance with an exemplary embodiment, the support may be a leg, knee support, a calf support, a rear support or a back support.

In accordance with another embodiment, there is provided a stretcher assembly including a frame, the membrane being in the form of a moulded support element or providing a plurality of belts.

BRIEF DESCRIPTION OF THE DRAWINGS

Embodiments of the present application are described below, by way of example only, with reference to the accompanying drawings, in which.

DESCRIPTION OF THE PREFERRED EMBODIMENTS

Described below are various embodiments of flexible patient supports comprising a stretchable membrane are is also designed to have sufficient load bearing properties to carry a patient's body weight or otherwise support at least a part of a patient's body. The supports may be useful in assisting a patient to rise from a reclined or sitting position to a standing position, and also for lifting and/or transporting a patient in a hospital or care home environment. Amongst the embodiments described below is a membrane which is at least partially stretchable and this may be made of a singular material or may have a multi-layer and/or multi-component construction, which structure is at least partially stretchable. It is envisaged that in most embodiments the membrane will stretch only a given amount under a given load and will remain flexible beyond such load. In an exemplary embodiment, the membrane has a sufficient thickness, tensile strength and modulus of elasticity to stretch when supporting the entirety of a patient's bodily weight, the upper torso of a patient and/or the force applied by a patient's knees and legs when moving from a sitting to a standing position without permanently deforming the membrane.

Figure 1:
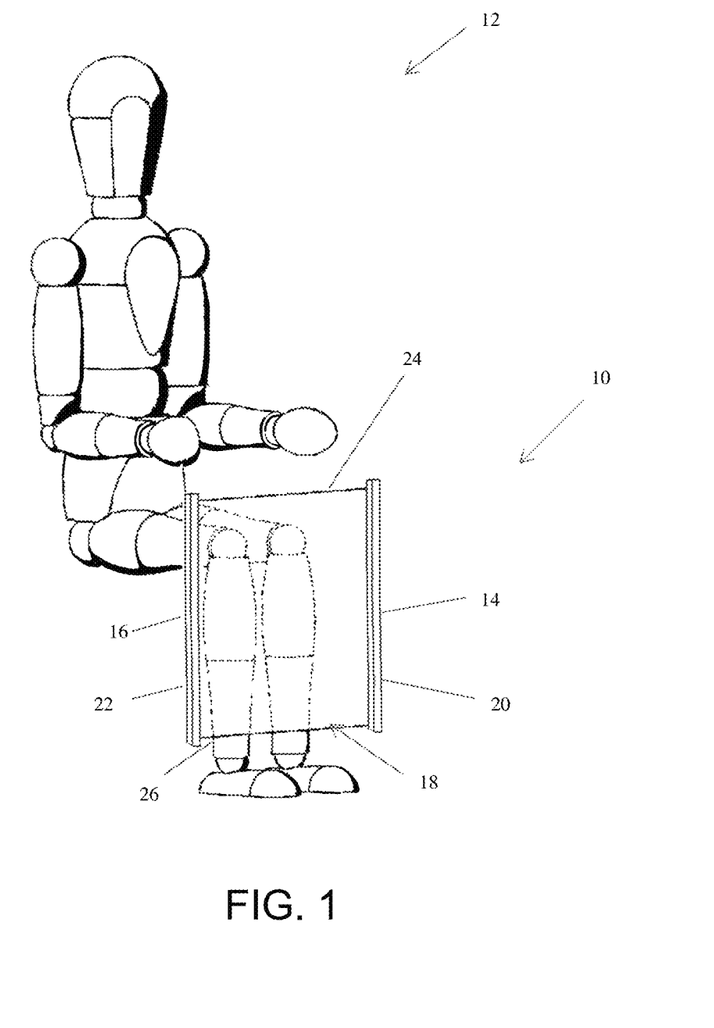
FIG. 1 shows a perspective front view of an exemplary embodiment of a patient support configured to support a patient's knees and legs.
Figure 2:
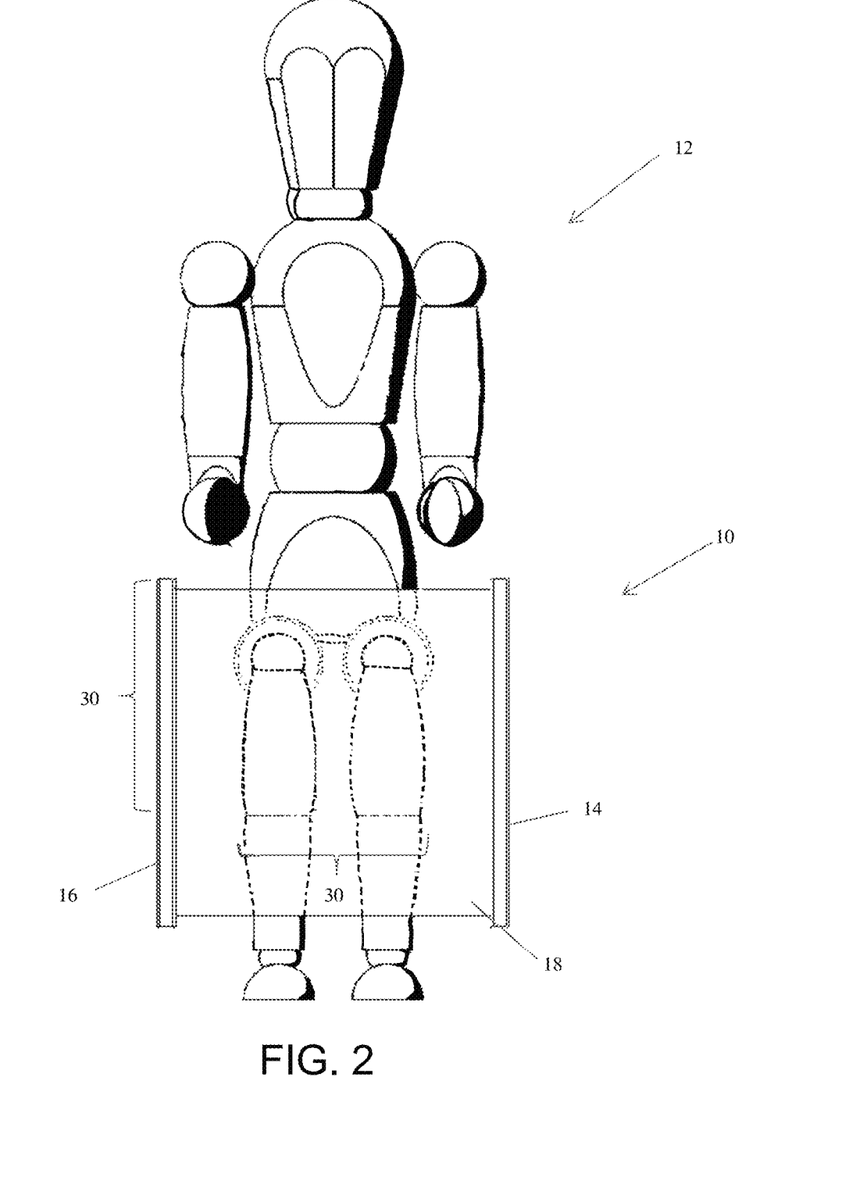
FIG. 2 shows a front view of the patient support of FIG. 1.
Figure 3:
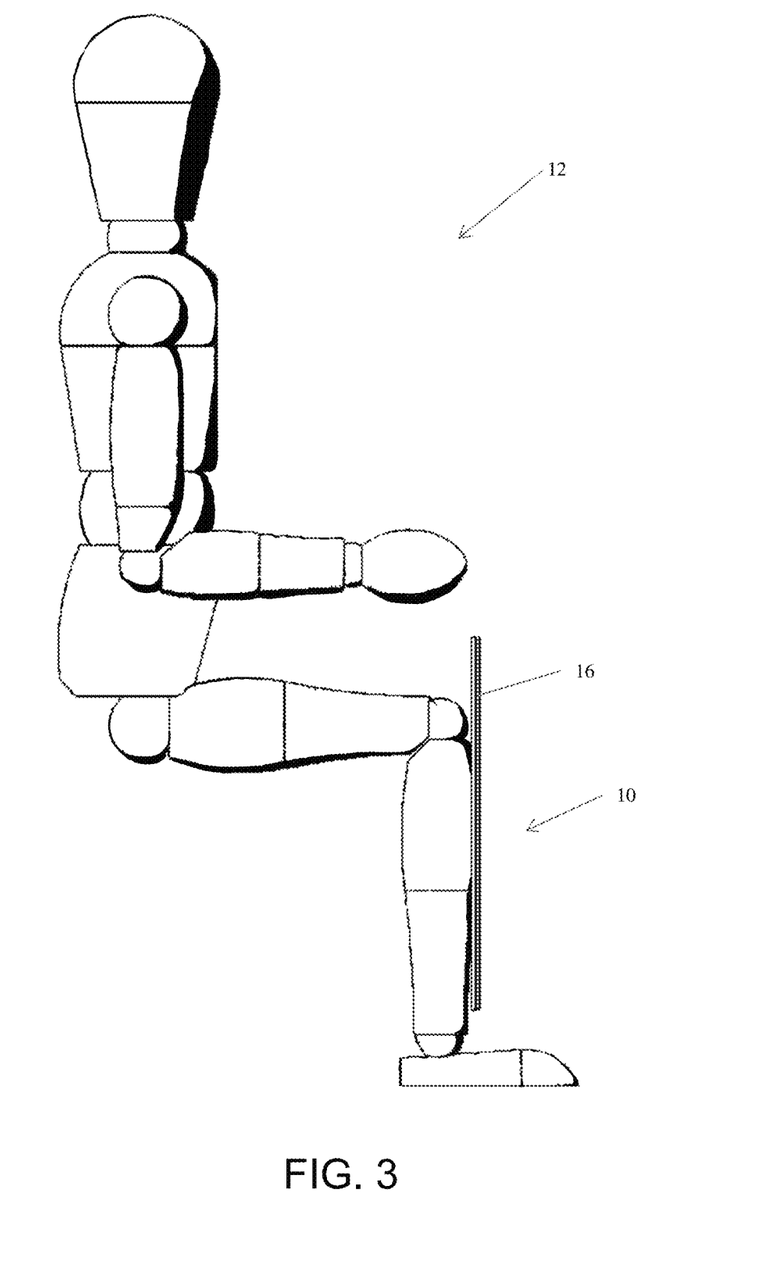
FIG. 3 shows a side view of the patient support of FIG. 1.

Referring to FIGS. 1 to 3, these show a first exemplary embodiment of patient support 10 configured as a leg support, for use in supporting the knee of a patient 12 and particularly for assisting the patient 12 to rise from a sitting to a standing position. The patient support 10 includes, in this example, first and second lateral support elements 14, 16, which may be configured as struts, forming a frame for positioning stretchable membrane 18 across a portion of a patient lifting device such as that described in U.S. Pat. No. 6,389,619, herein incorporated by reference in its entirety; lateral support 10 and stretchable membrane 19 may be arranged and positioned to function as the knee abutment of U.S. Pat. No. 6,389,619. In one embodiment, lateral support elements 14, 16 are bars or substantially rigid rods made of metal or other strong material. Stretchable membrane 18 may be positioned between and directly connected to the support elements 14, 16 such that stretchable membrane 18 is held taut, under tension. In another embodiment, stretchable membrane 18 may be positioned in a state of rest but full extended between lateral support elements 14, 16 such that there is no slack in stretchable membrane 18. First and second edges 20, 22 of the stretchable membrane 18 are attached to the frame in any suitable manner. They may, for example, be bonded or otherwise fastened to the frame, fixed within attachment elements of the lateral support 14, 16, adjustably positioned with respect to lateral supports 14, 16 or may be wrapped around the lateral supports and held by stitching or any other suitable method.

The stretchable membrane 18 may have a rectangular configuration with a width sufficient to accommodate both of a patient's legs and knees and for this purpose. In one embodiment, stretchable membrane 18 may have a width of about 50 to about 80 cm or so, although may be narrower or wider than this dependent upon the nature of the patient. In another embodiment, the stretchable membrane 18 may also have a length or may be positioned with respect to the ground such that it has a height of about 40 to about 70 cm.

In the exemplary embodiment shown in FIGS. 1-3, stretchable membrane 18 is only held by and is positioned along the entire length of its two lateral edges 20, 22 by lateral support elements 14, 16, while its top and bottom edges 24, 26 and the patient support surface of stretchable membrane 18 (as well as the face of stretchable membrane 18 opposing the patient support surface) defined by said edges are freestanding and unsupported, thus allowing the patient support surface of stretchable membrane 18 to flex and stretch in use without contacting any structures. Lateral support elements 14, 16 may form part of or may be connected to a sit-to-stand patient aid or other patient lift device, where patient support 10 is designed and configured to function as a knee support. Lateral support elements 14, 16 form a frame that supports edges 20, 22 of stretchable membrane 18 and allows the membrane patient support surface defined therebetween to freely stretch and move in a plane substantially orthogonal to the plane of lateral support elements 14, 16 without contacting a support structure. In another embodiment, top and bottom edges 24, 26 may also be connected to support elements that are the same as or similar to lateral support elements 14, 16 to further secure support stretchable membrane 18 to a patient lift and position support stretchable membrane 18 with respect to the patient lift and/or patient. In yet another embodiment, only opposing top and bottom edges 24 and 26 of stretchable membrane 18 may be attached or otherwise secured to a pair of support elements. In an exemplary embodiment, patient support 10 and stretchable membrane 18, has a sufficient thickness, tensile strength and modulus of elasticity to repeatedly stretch and absorb the force applied by a patient's bent knees and legs when the patient moves from a sitting to a standing position without permanently deforming stretchable membrane 18. The membrane may be sufficiently elastomeric to conform to and support the contacting portion of a patient's knees and legs pressing against stretchable membrane 18 at a point where maximum force is applied to stretchable membrane 18 during the sit to stand movement of the patient as well as when the patient retracts and straightens its knees and legs when moving into the standing position. The height of the stretchable membrane 18 may be sufficient and configured to extend from the top of the foot, around the ankle, to well above the knees of the patient and has a width sufficient to accommodate both of the patient's knees when sitting down on a chair and having his/her legs slightly apart.

As discussed above, it will be appreciated that the lateral supports 14, 16 would typically be a part of a larger item of equipment, such as a patient lift, in which the support elements 14, 16 are fixed so that these remain substantially rigid and steady during operation of the patient support 10. The skilled person will readily be able to appreciate the nature and structure of such equipment, being known in the art.

The stretchable membrane 18 may be made of silicone or other elastomeric material. In other specific embodiments, membrane 18 may be constructed from polyurethane, rubber or a rubber-like material. Stretchable membrane 18 may also be made of an elastic or other stretchable fabric material. In one example, stretchable membrane 18 may be constructed from a material that does not readily absorb liquids or form stains or may have a covering to facilitate cleaning.

Figure 9:
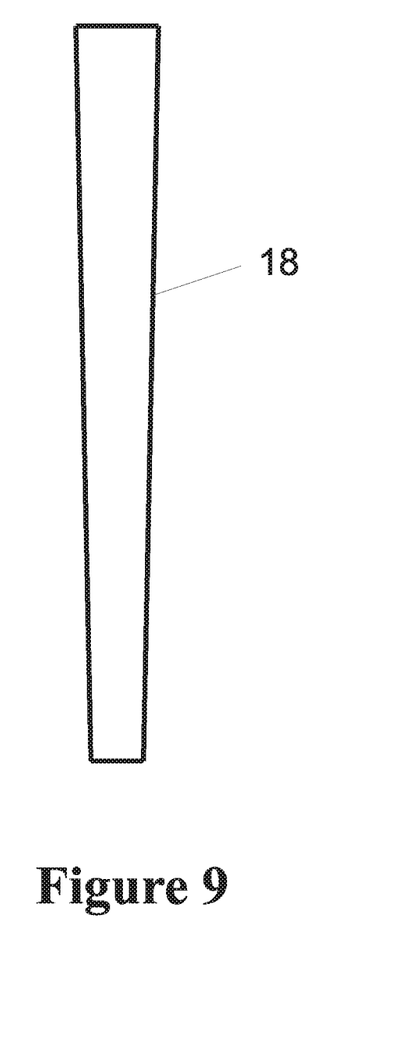
FIG. 9 shows a side view of the stretchable membrane of FIG. 1.

In some embodiments, the stretchable membrane 18 may be of substantially uniform thickness. In other embodiments, the stretchable membrane 18 may be provided with structural reinforcements, such as zones of thicker material, for instance in the regions where the patient's body part or parts are intended to press against the membrane for instance in the knee area 30 as shown in FIG. 2, in other embodiments being thicker in zones not contacted by the patient. Such reinforcement regions may be configured as strengthening bands. In other embodiments, the thicker zones of sheet material may extend over the whole of the relevant area of the stretchable membrane 18 (that is as depicted by zone 30 in FIG. 2) or may be in the form of ribs or other enforcement elements. It will be appreciated also that where ribs or other reinforcement elements are used, these may be of a different material to that of a membrane and need not necessarily be of stretchable material given their positioning on a stretchable substrate (the material of the stretchable membrane 18). As shown in FIG. 9, stretchable membrane 18 may also be graduated in thickness uniformly tapering from top edge 24 to a thinner bottom edge 26. In another embodiment, the upper portion of stretchable membrane 18 that is intended to come into contact with a patient's knees may be the region of stretchable membrane 18 having the greatest thickness.

The stretchable membrane 18 could be provided with signs, symbols or letters, which in some embodiments may be embossed or recessed into the material of the stretchable membrane 18. These could include, for example, product name, product characteristics and/or operating specifications, washing instructions, company logo, company name and any combinations of these.

The stretchable membrane 18 may be of any colour and in some embodiments it may be transparent or translucent so that a care worker can see, from the other side of the membrane, where a patient's knees, in this example, are positioned with respect to the membrane and in particular the contact area 30.

The knee support 10 shown in FIGS. 1 to 3 provides for support to a patient's knees/legs, against which the patient 12 can press as the patient rises from a seating position. The stretchable membrane 18, attached to the lateral supports 14, 16, will take the force of the patient's legs during this movement and will in the first instance stretch to provide a soft cushioning function to the support 10. Once the stretchable membrane 18 has stretched beyond its initial stretch, it will provide an increasing restraining force to support the patient's legs and knees, thereby helping the patient reach a standing position. During this action, the stretch of the stretchable membrane 18 also assists in holding the patient's knees, by partially wrapping around the knees, which can reduce the chance of slippage of the patient.

The patient support 10 could also be positioned behind a patient's calves in order to support the calves and prevent slippage of the patient's feet. For this purpose, the support unit 10 could be made to have a length or be positioned to have a height with respect to the ground of less than the top of a patient's lower leg. In one embodiment, it may have a length or may be positioned to have a height with respect to the ground of no more than about 10 to about 50 cm.

Figure 4:
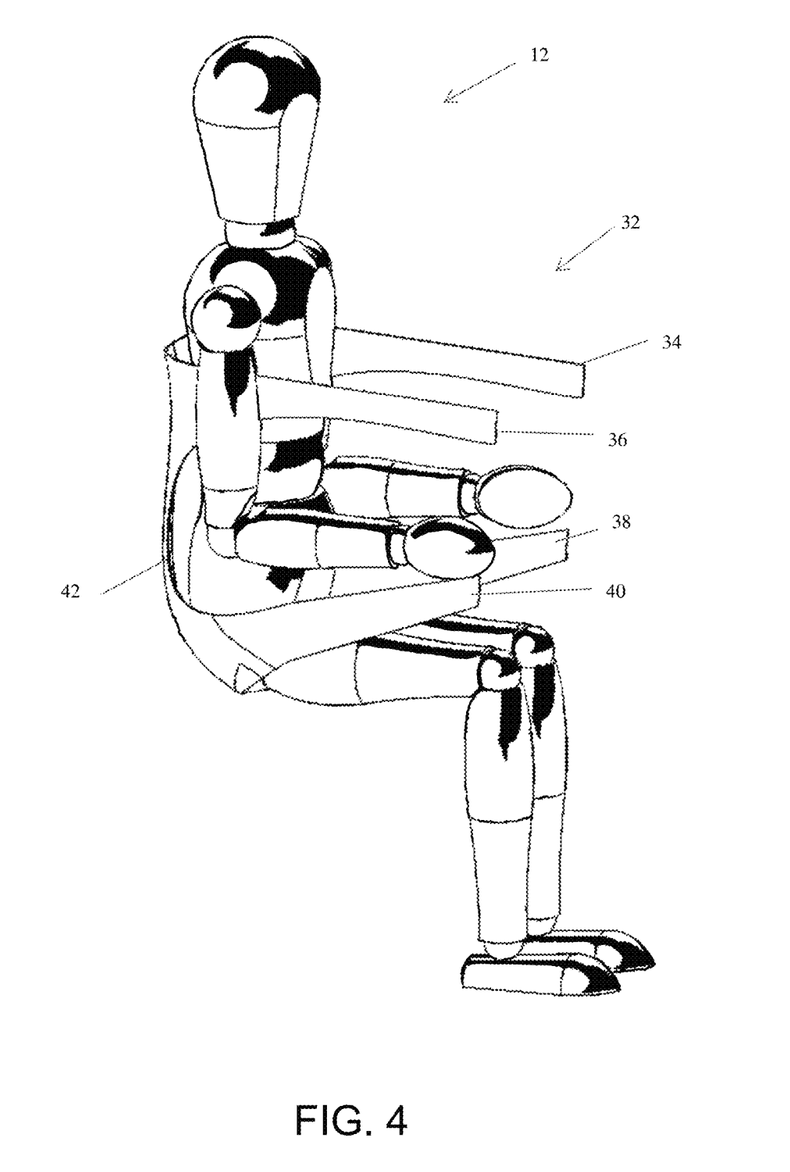
FIG. 4 shows a side view of a second exemplary embodiment of a patient support for a patient's back and rear.
Figure 5:
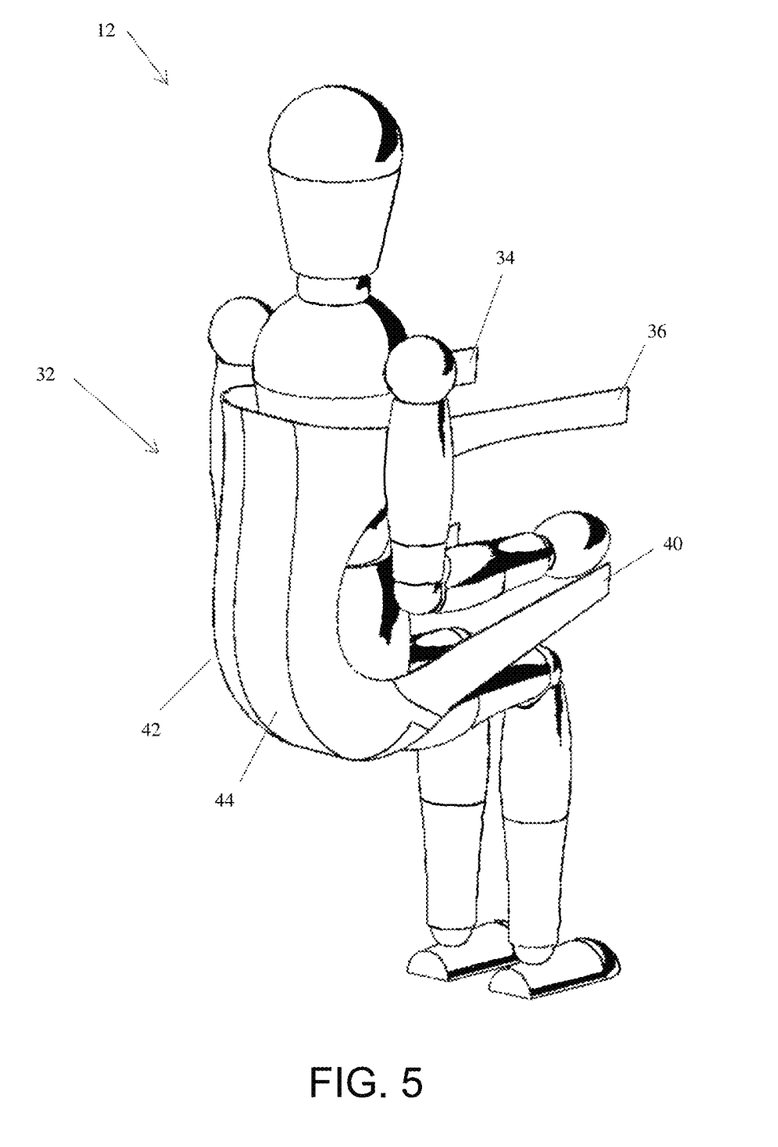
FIG. 5 shows a perspective rear view of the patient support of FIG. 4.

Referring now to FIGS. 4 and 5, these show another embodiment of patient support 32 constructed from a support membrane 42, which in this case is a rear and trunk support, again made of silicone or any of the other materials disclosed herein, including the materials of membrane 18. The patient support 32 includes first and second torso straps 34, 36 and first and second seat straps 38, 40. The straps will typically be provided with couplings such as hooks, rings or other fasteners, for attachment to a harness of known type. The patient support 32 also includes a seat and trunk support membrane 42 which is shaped to support the patient's back and rear in a seated position, as shown in FIG. 5. In one embodiment, support membrane 42 may have an L-shaped shaped configuration, with a substantially rectangular upper region and a curved lower portion adapted to support and receive the rear and/or a portion of the thighs of a patient in a seated position.

At least the support membrane 42 is made of a stretchable material; straps 34-40 may also be made of the same material. It will be appreciated though, that in some embodiments the straps 34, 36, 38, 40 could be made of a non-stretchable material if desired. The use of stretchable material to construct patient support 32 and support membrane 42 imparts an elastic characteristic to the device, allowing it to stretch when subjected to load. Such give, or elasticity, increases patient comfort particularly in comparison with existing stiff and rigid devices which can be uncomfortable. Furthermore, the elasticity of the membrane assists in conforming to the contours of the patient to better secure and support the patient, which can reduce the chance of slippage of the patient during handling.

In an exemplary embodiment, support membrane 42 may include a strengthening band 44 extending along a length of the support membrane 42. As explained above, this reinforcement region or strengthening band 44 may be a region having a greater membrane thickness or may be provided with ribs or other reinforcement elements, again as described above. The support membrane 42 may be made of a plurality of different thicknesses and in some embodiments may have a variable thickness across its extent. In one embodiment, support membrane 42 and patient support 32 may be constructed from three portions extending along the length of support membrane 42 in which a strengthening band 44 is centrally positioned between and connects two adjoining support membrane portions positioned on either side of strengthening band 44. Straps 34, 36, 38, 40 may extend from opposing corners of the two support membrane portions and may be sized and configured to wrap around and secure a patient's upper and lower torso. Patient support 32 and support membrane 42 may have a sufficient thickness, tensile strength and modulus of elasticity to repeatedly stretch and conform to a patient's body contours in a sitting position as well as support the entirety of a patient's bodily weight to lift and transport a patient without permanently deforming.

The support membrane 42 may have a sufficient length and may further be positioned with respect to the patient that it covers the patient's head and extends low enough so as to support the back of the patient's thighs. It will be appreciated that patient support 32 provides more harness attachment points than existing supports.

As with the embodiments of FIGS. 1 to 3, the patient support 32 may be made of any colour or may be transparent or translucent and may be provided with signs, symbols or letters thereon.

In an exemplary embodiment, the patient support 32, as with all the supports disclosed herein, has no stitching of the membrane at least at those parts of the membrane which are likely to contact the patient 12. Stitching can make the device stiffer and provide protrusions or areas of hardness which are uncomfortable to the patient. The use of any of the materials disclosed above for the patient support 32 can avoid use of the stitching.

Figure 6:
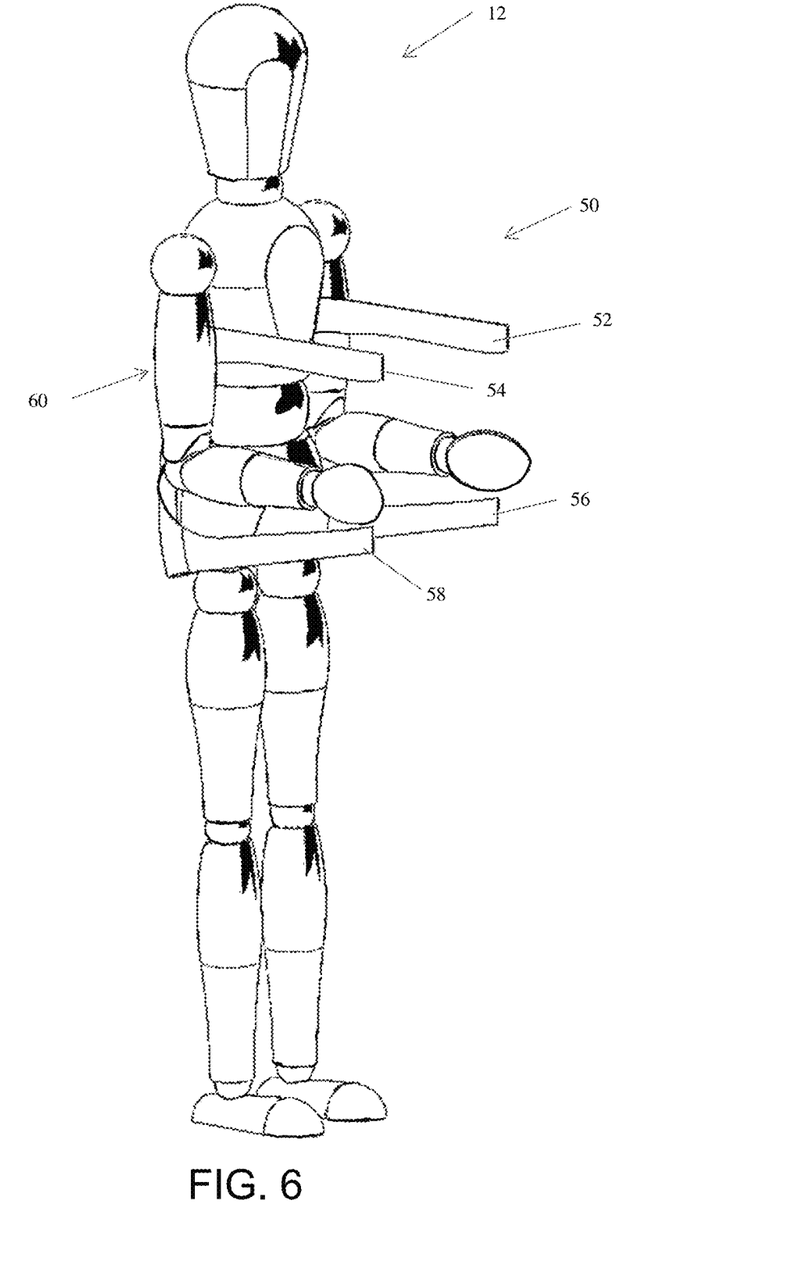
FIG. 6 shows a side view of a third exemplary embodiment of a patient support configured as a back support.
Figure 7:
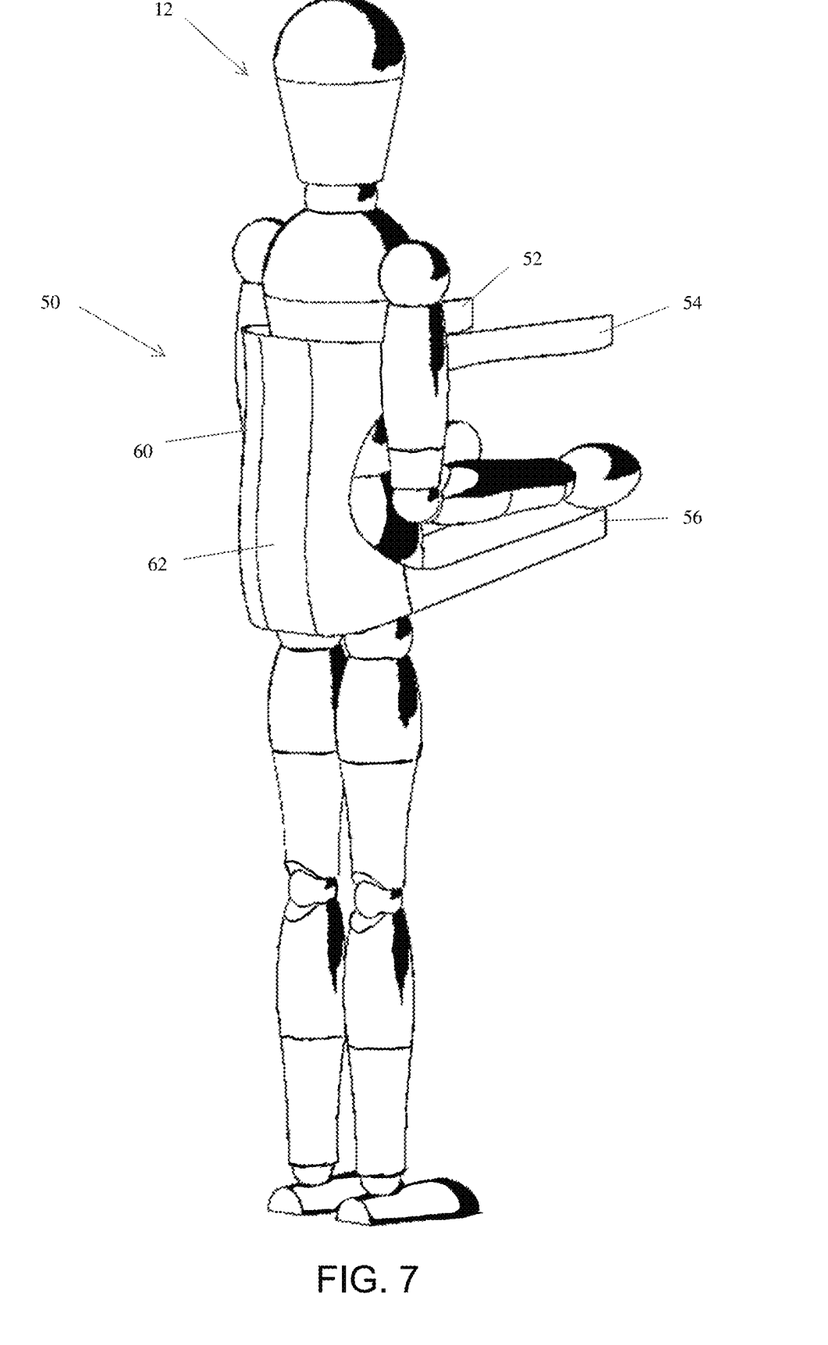
FIG. 7 shows a perspective rear view of the patient support of FIG. 6.

Referring now to FIGS. 6 and 7, these show another embodiment of patient support 50, which in this case is configured as a back support. This embodiment of patient support 50 may be configured to be positioned about a patient's back and used for assisting a patient 12 to rise from a sitting position to a standing position.

The patient back support 50 may include four strap elements 52, 54, 56, 58 at adjacent sides and at the top and bottom of a support membrane 60 which covers a patient's back and may be used to secure the patient's upper and lower torso, as can be seen in FIG. 7. Straps 52, 54, 56, 58 may be located at opposing corners of patient back support 50 and support membrane 60 and may be configured in a similar manner and constructed form the same material as the straps 34, 36, 38, 40. Support membrane 60 may have a substantially rectangular configuration configured to cover and conform to a patient's back and may be constructed from the same material and constructed in the same manner as support membrane 42. As shown in FIG. 7, support membrane 60 may also have a strengthening band 62 or other reinforcement elements as discussed above, extending along a length of patient back support 50 in a similar manner as that described in the embodiment of FIGS. 4-5. This reinforcement region or strengthening band zone 62 may have a greater thickness or other strengthening elements of the types described above.

The patient back support 50 shown in FIGS. 6 and 7 may have the same features as the supports disclosed above and in particular the rear and trunk patient support 32 shown in FIGS. 4 and 5. Patient back support 50 and support membrane 42 may have a sufficient thickness, tensile strength and modulus of elasticity to repeatedly stretch and conform to a patient's back and torso as well as and/or support the weight of a patient's upper torso and withstand the force necessary to lift a patient from a sitting to a standing position without permanently deforming the support membrane 42.

The patient back support 50 may have a height such that it reaches above the patient's head and low enough to align with the patient's tail bone although, as with the other embodiments disclosed herein may have different dimensions.

As with the rear and trunk patient support 32, the patient back support 50 may have a membrane which is generally pre-curved or shaped to the patient although this is not necessary.

It is to be appreciated that the embodiments of support shown in FIGS. 4 to 7 and associated embodiments are not restricted to having four straps as they may have more than four and in some cases fewer than four.

The patient support may have many other configurations. One example is a rear support shaped and sized to support a patient's rear and having straps for attachment to a harness. Again, the rear support may have four straps as with the embodiments of FIGS. 4-7. Such a support could extend up to above the patient's waist and sufficiently to touch the back of the patient's thighs.

Figure 8:
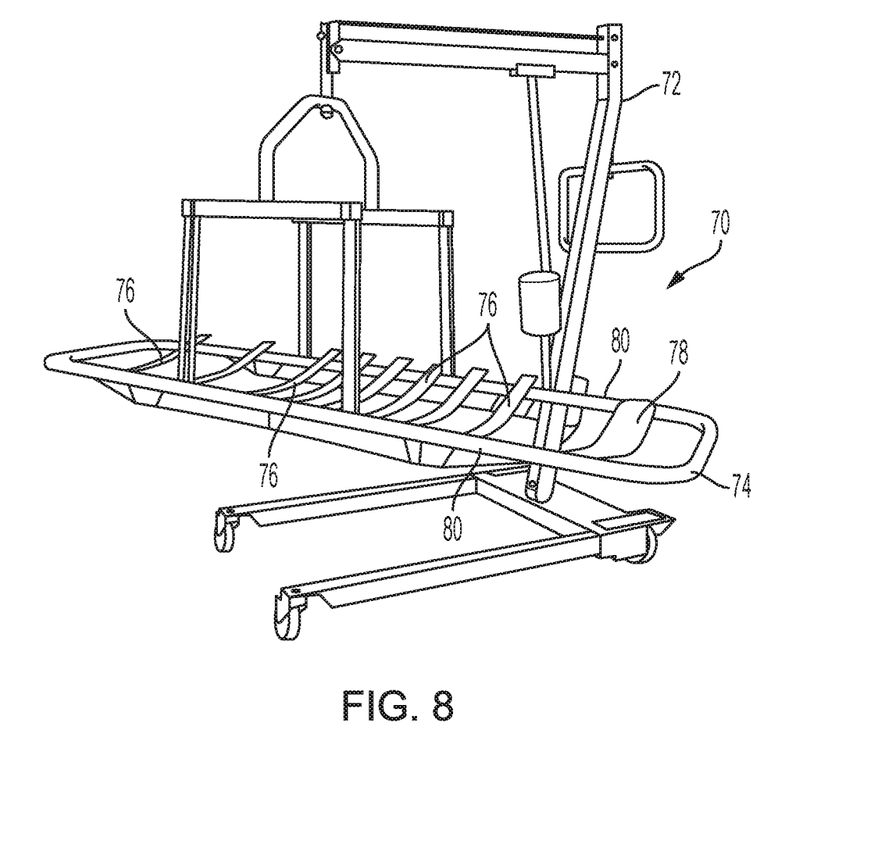
FIG. 8 shows a perspective view of third exemplary embodiment of a patient support.

Referring now to FIG. 8, there is shown an example of a stretcher frame assembly 70 according to another embodiment of the application. The stretcher frame assembly 70 is shown coupled to a hoist 72 of conventional form and therefore not described herein in detail.

The stretcher frame assembly 70 includes a generally rectangular open frame element 74, again of conventional form, which has a shape and size larger than the frame of a typical patient, such that a person carried by the frame assembly 70 can lie comfortably within the frame element 74.

Coupled to the frame element 74, in this embodiment, there is provided a series of straps 76, 78 which extend from one frame side 80 to the other and are attached to the frame sides 80 by any suitable mechanism of which several will be apparent to the skilled person. One or more of the straps 78 may be wider and/or thicker than the other straps 78, for instance to support a heavier part of a patient, typically the head, patient's seat and so on. The straps will be made from the membrane taught herein, that is of stretchable material and may have all of the characteristics of the membrane taught herein. The provision of straps 76, 78 made of such membrane will allow the straps and hence the patient support to stretch controllably at the start of a support operation, that is when the patient is lowered onto the stretcher or the stretcher is raised from a ground or other support surface, providing in effect a soft contact, and will also enable to straps to conform better to the shape of the patient.

Other embodiments provide in place of the straps 76, 78, the frame assembly 70 could be provided with a support element in sheet form which extends across the entirety of or substantially the entirety of the space within the frame 80. Such a support element may be a moulded support, sometimes referred to as a shovel, formed of the membrane material taught herein. The support will thus have the same characteristics as taught herein. The membrane or shovel could have zones of different thickness, again as taught herein.

The stretcher can be used for carrying an injured patient. The arrangement can be such that the straps 76, 78 or shovel can be slid under the laying patient and then attached to the stretcher frame, so that the patient can then be raised off the ground. The stretcher can thus be used for assisting the transfer of a patient or animal that has fallen and possibly suffered back or neck injuries.

All of the embodiments of patient support described above and contemplated by the teachings herein are able to spread pressure much more efficiently than stiff supports made of metal, tough fabric or other similar materials, in particular as the result of the stretchability of the membrane. Furthermore, the membrane will not cut into a patient's flesh in the same manner as prior art supports.

Moreover, when raising a patient, the patient support can apply what could be described as a slow start to the patient's movement as the result of stretching of the membrane, which not adds comfort to the patient. Conventional slings and other supports are not able to provide such a "soft start" due to their rigidity, firmness and inelasticity.

The support taught herein can also be used for patient rehabilitation, for example enabling a patient to carry out sit-to-stand movements as well as stand-to-sit movements making use of the patient support, which will not be uncomfortable or painful to use as the material of the membrane 18 will stretch and flex at the same location of flexure of the patient's body. The support can also flex while the patient is standing, enabling the patient to relax more when upright. It is envisaged that the support could also be used to enable natural gait training. The support could be used as a training device, in which a patient can press against the support with comfort, with the membrane flexing to provide counter force and thus exercising for the patient.

When the membrane 18 is formed of silicone or similar material, the material will provide a certain amount of friction which can help in preventing slippage of the patient during movement. Moreover, the resilient nature of the membrane 18 can enable the support to be used by different patients without having to make any adjustments given that the membrane will stretch less or more in dependence upon the force applied to it. Similarly, the material of the membrane, particularly made of silicone or similar material can contour to the shape of the body and do so significantly better than stiff fabric slings.

The skilled person will appreciate that only some embodiments contemplated by teachings herein are described above and that other designs of the patient support will be ready apparent to the skilled person.

It is also to be understood that the various features of the different embodiments disclosed herein may be used interchangeably from one embodiment to another.

The invention claimed is:

1. A patient support comprising a support for a patient's knees or legs, against which the patient can press as the patient rises from a seating position to a standing position, the support including a support structure and at least one support membrane connected to the support structure, the at least one support membrane configured to assist the patient in rising from the seating position to the standing position during which a front side of the patient's knee or leg is pressed against the at least one support membrane, the at least one support membrane being entirely made of a stretchable material, the at least one support membrane is graduated in thickness by uniformly tapering from a top edge of the at least one support membrane to a thinner bottom edge of the at least one support membrane.

2. The patient support according to claim 1, wherein the at least one support membrane is formed of sheet material.

3. The patient support according to claim 1, wherein the at least one support membrane is in the form of a sheet, strap or shovel.

4. The patient support according to claim 1, wherein the at least one support membrane is formed from silicone, polyurethane, thermoplastic polyurethane (TPU), a thermoplastic elastomer (TPE), rubber or a rubber-like material.

5. The patient support according to claim 1, wherein the at least one support membrane is formed from a stretchable fabric.

6. The patient support according to claim 1, wherein the at least one support membrane is formed from a material exhibiting a variable coefficient of stretch.

7. The patient support according to claim 1, wherein the at least one support membrane is formed from a material exhibiting at least two coefficients of stretch.

8. The patient support according to claim 1, wherein the at least one support membrane is connected to the support structure only at edges or extremities thereof.

9. The patient support according to claim 1, wherein the at least one support membrane is free to flex on the support structure.

10. The patient support according to claim 1, wherein the support structure provides a lateral frame across which the at least one support membrane is connected.

11. The patient support according to claim 10, wherein the lateral frame includes first and second side elements to which the at least one support membrane is connected.

12. The patient support according to claim 11, wherein edges of the at least one support membrane between the lateral frames are able to flex.

13. The patient support according to claim 1, wherein at least contact zones of the at least one support membrane are free of stitching.

14. The patient support according to claim 1, wherein the support includes a calf support.

15. A patient support comprising:
    a support structure comprising first and second support members spaced from one another to form a frame; and
    a support membrane directly connected to and extending between the first and second support members such that the support membrane is held under tension, the support membrane configured to assist a patient in rising from a seating position to a standing position during which a front side of a patient's knee or leg is pressed against the at least one support membrane, the support membrane being graduated in thickness by uniformly tapering from a top edge of the support membrane to a thinner bottom edge of the support membrane,
    wherein the support membrane is transitionable between a first position and an extended second position,
    wherein, when in the first position, the support membrane is held between the first and second support members, and
    wherein, when in the second extended position, at least a portion of the support membrane stretches and transitions away from a plane extending between the first and second support members.

16. The patient support as claimed in claim 15, wherein the support membrane comprises a stretchable silicone material.

17. The patient support as claimed in claim 15, wherein the support membrane is sufficiently elastomeric to conform to and support a contacting portion of a patient's knees and legs pressing against the support membrane.

18. The patient support as claimed in claim 15, wherein a height of the support membrane is configured to extend from a top of a patient's foot to above the patient's knees.

19. A patient support comprising a support for a patient's knees or legs, against which the patient can press as the patient rises from a seating position to a standing position, the support including a support structure and at least one support membrane connected to the support structure, the at least one support membrane configured to assist the patient in rising from the seating position to the standing position during which a front side of the patient's knee or leg is pressed against the at least one support membrane, the at least one support membrane having a thickness that increases gradually and uniformly from a bottom edge of the at least one support membrane to a top edge of the support membrane.

20. The patient support of claim 19, wherein the patient support is a free-standing structure.

* * * * *